United States Patent
Rivera (12)

(10) Patent No.: US 6,328,967 B1
(45) Date of Patent: Dec. 11, 2001

(54) DELIVERY SYSTEM TO MODULATE IMMUNE RESPONSE

(75) Inventor: Roberto L. Rivera, Cincinnati, OH (US)

(73) Assignee: Allergenics, Inc., So. San Francisco, CA (US)

( * ) Notice: Subject to any disclaimer, the term of this patent is extended or adjusted under 35 U.S.C. 154(b) by 0 days.

(21) Appl. No.: 09/041,514

(22) Filed: Mar. 12, 1998

(51) Int. Cl.[7] .................. A61K 39/385; A61K 45/05; A61K 47/00; A61K 51/12; A61K 9/52; A61K 9/14; A61K 9/50

(52) U.S. Cl. ................. 424/184.1; 424/426; 424/434; 424/439; 424/451; 424/457; 424/461; 424/463; 424/489; 424/491; 424/492; 424/493; 514/13

(58) Field of Search .................. 514/13; 424/184.1, 424/426, 434, 439, 451, 457, 461, 463, 489, 491, 492, 493

(56) References Cited

U.S. PATENT DOCUMENTS

| | | | |
|---|---|---|---|
| 5,417,986 | * | 5/1995 | Reid et al. . |
| 5,591,433 | | 1/1997 | Michael et al. .................. 424/184.1 |
| 5,629,001 | * | 5/1997 | Michael et al. . |

FOREIGN PATENT DOCUMENTS

| | | | |
|---|---|---|---|
| 0 603 992 A1 | 6/1994 | (EP) | ............................ A61K/9/50 |
| 2723849 A | 3/1996 | (FR) | ............................ A61K/39/00 |
| 1287032 A | 11/1989 | (JP) . | |
| WO94/23738 | 10/1994 | (WO) . | |

OTHER PUBLICATIONS

Rock, et al., Analysis of the Role of MHC Class II Presentation in the Stimulation of Cytotoxic T Lymphocytes by Antigens Targeted into the Exogenous Antigen–MHC Class I Presentation Pathway, Journal of Immunology, American Association of Immunologists, 1996, p.3721–3726 .

Vidard, et al., Analysis of MHC Class II Presentation of Particulate Antigens by B Lymphocytes, The Journal of Immunology, American Association of Immunologists 1996, p.2809–2818.

Irache, et al., Bioadhesion of Lectin–Latex Conjugates to Rat Intestinal Mucosa, Pharmaceutical Research vol. 13, No. 11, 1996, p.1716–1719.

Robbins–Roth, Cynthia, Cancer Vaccines: Are we finally on the right track?, Bioventure View, vol. 12, No. 18, 1997, p. 1, 2, 4–10.

Schipper et al., Chitosans as Absorption Enhancers for Poorly Absorbable Drugs 2: Mechanism of Absorption Enhancement, Pharmaceutical Research, vol. 14, No. 7, 1997, p.923–929.

Disis, Mary L. et al., High–Titer HER–s/neu Protein–Specific Antibody Can Be Detected in Patients With Early–Stage Breast Cancer, Journal of Clinical Oncology, vol. 15, No. 11 (Nov.), 1997: p. 3363–3367.

Mowat, et al., Immune–stimulating complexes containing Quil A and protein antigen prime class I MHC–restricted T lymphocytes in vivo and are immunogenic by the oral route, Immunology 1991 72 317–322.

Maloy, et al., Induction of mucosal and systemic immune responses by immunization with ovalbumin entrapped in poly(lactide–co–glycolide) microparticles, Immunology 1994 81 661–667.

Rock, et al., Inhibition of Class I and Class II MHC–Restricted Antigen Presentation by Cytotoxic T Lymphocytes Specific for an Exogenous Antigen, The Journal of Immunology, 1992, vol. 148, p. 3028–3033.

Kotze, et al., N–Trimethyl Chitosan Chloride as a Potential Absorption Enhancer Across Mucosal Surfaces: In Vitro Evaluation in Intestinal Epithelial Cells (Caco–2), Pharmaceutical Research, vol. 14, No. 9, 1997, p. 1197–1202.

Disis, et al., Peptide–Based, but Not Whole Protein, Vaccines Elicit Immunity to HER–s/neu, an Oncogenic Self–Protein, The Journal of Immunology, 1996, p.3151–3158.

Reid, George, Soluble proteins incorporate into ISCOMs after covalent attachment of fatty acid, Vaccine, 1992, vol. 10 No. 99 p.597–602.

* cited by examiner

*Primary Examiner*—Geetha P. Bansal
(74) *Attorney, Agent, or Firm*—Townsend & Townsend & Crew

(57) ABSTRACT

A microsphere containing an immunogen bound to an inert particle having a mesh size of greater than about 35 mesh for site-specific release and induction of an immune response. The immune response may be an overall enhanced T lymphocyte immune response or a selective response. The physical and chemical characterigticg and/or modes of administration of the microsphere may be engineered to increase $T_H1$ lymphocytes for treatment of cancer or infectious disease. The microencapsulated immunogen has an enteric coating for oral administration.

18 Claims, 3 Drawing Sheets

DELIVERY SYSTEM TO MODULATE IMMUNE RESPONSE

FIELD OF THE INVENTION

This invention is directed generally to a method of selecting and/or selectively modulating an immune response by administering a microencapsulated immunogen.

BACKGROUND OF THE INVENTION

The immune system recognizes and distinguishes substances as self versus nonself, and defends the body against nonself substances. The importance of this distinction is evident in a variety of conditions such as autoimmune diseases, rejection of transplanted tissues or organs, allergic reactions, cancer and infectious diseases, and modes of treatments such as immunotherapy and gene therapy. For example, in autoimmune diseases such as rheumatoid arthritis, systemic lupus erythematosus and myasthenia gravis, the body mistakenly treats self as nonself and thus destroys its own components. In transplant rejection, immunosuppressive drugs are administered to a recipient to prevent the recipient's immune system from rejecting a true nonself substance so that the recipient can accept the transplanted tissue or organ as its own. In allergic reactions such as asthma, eczema and hay fever, there is an immune hypersensitivity in some individuals that occurs immediately following contact with an antigen. In infectious diseases a microbe such as a bacterium, parasite or virus stimulates an immune response. The microbe or a microbe subunit may be formulated as a vaccine to provide prophylactic protection against subsequent infection. In cancer, unlike the other conditions, an immune response is not mounted and the lack of an immune response plays a role in the uncontrolled growth of malignant cells. A wide variety of foreign substances, termed antigens or immunogens, elicit an immune response and thus are targeted by the immune system. Examples of antigens include, but are not limited to, infectious disease agents such as bacteria, viruses, parasites and fungi as well as mites, pollen, animal dander, drugs, toxins and chemicals.

The immune system is a complex network of cells, tissues and organs that directly and indirectly target and ultimately destroy foreign substances. Of the various cells involved in mounting an immune response, lymphocytes are one type of white blood cells that have a crucial role. One type of lymphocyte is the B lymphocyte (B cell) that targets and indirectly destroys foreign substances by mounting a humoral immune response to produce antibodies against specific antigens. The other type of lymphocyte is the T lymphocyte (T cell) that targets and directly kills foreign substances by mounting a cell-mediated immune response. There are three major subtypes of T cells designated as T helper cells, T suppressor cells, and T cytotoxic cells. T helper cells are of two types: $T_H1$ and $T^H2$ cells. $T^H2$ cells help B cells mount a humoral immune response and help T cytotoxic cells maintain themselves by producing growth factors needed by the T cytotoxic cells. $T^H2$ cells express the CD4 glycoprotein antigen. T suppressor cells inhibit or suppress T helper cells; they express the CD8 glycoprotein antigen. T cytotoxic cells, also called cytotoxic T lymphocytes (CTL), express the CD8 glycoprotein antigen and are a subset of T cells that kill cells expressing a specific antigen upon direct contact with these target cells. Pre-CTL are T cells that are committed to the CTL lineage, have undergone thymic maturation and are already specific for a particular antigen, but lack cytolytic function. CTL are important effector cells in three settings: (1) intracellular infections of non-phagocytic cells or infections that are not completely contained by phagocytosis such as viral infections, (2) infections by bacteria such as *Listeria monocytogenes*, and (3) acute allograft rejection and rejection of tumors.

An immunogenic response is most predictably induced by using a protein as the immunogen. In immunotherapy, the protein is frequently administered parenterally, for example by injection. While injections are inconvenient and uncomfortable to many patients, they have heretofore been a common route of administration because orally administered protein is degraded by protease enzymes and acid in the stomach and enzymes in the small intestines. It has been demonstrated that oral administration of a soluble protein such as the model antigen ovalbumin (OVA) results in the induction of immune tolerance, characterized by the loss of either antibody or T cell response to the protein antigen. However, U.S. Pat. No. 5,591,433 discloses that immunologically active biomolecules and other therapeutic proteins can be orally administered by microencapsulating the protein and coating the microsphere to form a pH-sensitive enterocoated microsphere particle that is resistant to the action of digestive proteolytic enzymes and acids. The microspheres disclosed in the '433 patent consist of protein bound to an inert particle having a mesh size of about 30–35 mesh (about 600 $\mu$m to about 500 $\mu$m) diameter and coated with an acid stable polymer. What is needed, however, is a method of better selecting and selectively modulating a particular immune response from the complex immune repertoire to better respond to different antigenic stimuli in different conditions requiring treatment.

For example, current cancer treatments include combinations of chemotherapy, radiation therapy, and surgical excision of some or all of a solid tumor. Each of these treatment mechanisms is targeted to eliminating malignant cells but is performed at the expense of destroying nonmalignant cells. Thus, none of these treatments utilize the body's own capacity for cell destruction, namely, the immune system and particularly the cytotoxic T cells, to kill malignant cells. A method of increasing an immune response and/or selectively stimulating the cytotoxic T cell population would therefore be a valuable supplement to traditional treatment methods. In addition, such a method would operate without the adverse effects of chemotherapeutic drugs, radiation, or surgical insult. Cancer cells, however, are not recognized as foreign by the immune system and thus are not targeted for destruction. One goal in developing cancer treatments is to stimulate the immune system to mount an immune response against cancer cells. Of the three major T cell types, the T cytotoxic cells frequently directly target and destroy cancer cells. Thus, selectively increasing the T cytotoxic cell subtype may be an advantageous way to check the unregulated cell division that is a hallmark of cancer cells.

As another example, the T cytotoxic cells also directly target and destroy extracellular infectious disease agents and infectious disease agents in infected cells. Cell mediated immunity consists of two types of reactions. The first type is macrophage activation resulting in the killing of phagocytized microbes. The second type is lysis of infected cells by CD8+ cytotoxic T lymphocytes (CTL). Differences among individuals in the patterns of immune responses to intracellular microbes, for example in HIV infection, are important determinants of disease progression and clinical outcome. The selective increase in the T cytotoxic cell subtype may be used to combat infectious diseases.

There is thus a need for a method and composition to better modulate and/or selectively stimulate an immune response. Such a method and composition would find wide use in immunotherapy or gene therapy for conditions such as allergies, infectious diseases, cancer, transplant rejection, and autoimmune diseases. Such a method and composition would also be a valuable prophylactic and/or therapeutic supplement to current methods of treating these conditions.

SUMMARY OF THE INVENTION

This invention provides methods and compositions to induce an enhanced general or selective immune response. An Immynogen delivery system comprises a microsphere of an immunogen bound to an inert particle having a mesh size greater than about 35 mesh. The microsphere is administered to the small intestine of a mammal. The microsphere is preferably administered orally and contains one or more enteric coatings and may be administered in a gel capsule. In one embodiment the inert particle has a mesh size greater than about 40 mesh and may be a nonpareil, a silica powder, a salt crystal or a sugar crystal.

The response may encompass a general enhanced production of $T_H1$ cells, $T_H2$ cells and cytotoxic T lymphocyte (CTL) subsets, or an enhanced shift from a $T^H2$ type response to a $T^H1$ type response, or an enhanced shift from a $T_H1$ type response to a $T^H2$ type response, or an enhanced differentiation of pre-CTL to CTL. The immunogen may be a peptide, a protein fragment, a protein, a DNA, and/or an RNA, and may be a gene, a gene fragment or a vaccine.

The immunogen may be administered in a dosing regimen and/or a dosing composition containing a number of microspheres to selectively induce a particular immune response. The microspheres of the dose may contain the same enteric coatings or different enteric coatings, the same formulation or different formulations, and/or the same inert particle core composition and size or different core compositions and sizes. The immunogen may also be administered with a potentiating agent, either in a single inert particle or in separate inert particles. If formulated with the immunogen and potentiating agent in a single inert particle, the various single inert particles of the administered dose may have the same enteric coating or a different enteric coating, the same formulations or different formulations, and/or the same inert particle core composition and size or different core compositions and sizes. Likewise, if formulated with the immunogen and potentiating agent in separate inert particles, the separate microspheres of the administered dose may have the same enteric coatings or different enteric coatings, the same formulations or different formulations, and/or the same inert core compositions and sizes or different core compositions and sizes.

As will be appreciated, the disclosed delivery system and methods of using the system have a wide array of applications. These and other advantages of the invention will be further understood with reference to the following drawings, detailed description and examples.

DETAILED DESCRIPTION OF THE INVENTION

Definition of Terms

Figure 1:
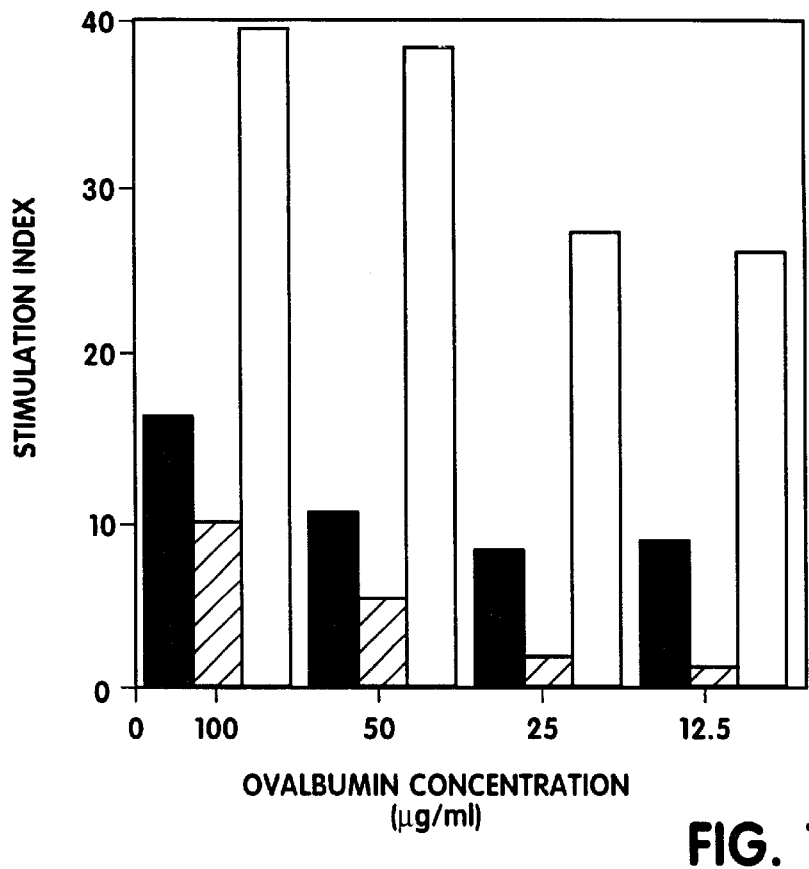
FIG. 1 is a graph of the results of primary lymphocyte proliferation with different modes of ovalbumin (OVA) administration.

The terms immunogen or antigen are broadly used herein to encompass any chemical or biological substance that elicits an immune response when administered to a mammal. While an immunogen is frequently a protein, it may also be a nucleic acid. For the purpose of the present invention, immunogens include but are not limited to the following: allergenic proteins and digested fragments thereof such as pollen allergens from ragweed, rye, June grass, orchard grass, sweet vernal grass, red top grass, timothy grass, yellow dock, wheat, corn, sagebrush, blue grass, California annual grass, pigweed, Bermuda grass, Russian thistle, mountain cedar, oak, box elder, sycamore, maple, elm and so on, dust, mites, bee and other insect venoms, food allergens, animal dander, microbial vaccines which in turn include viral, bacterial, protozoal, nematode and helminthic vaccines and their various components such as surface antigens, including vaccines which contain glycoproteins or proteins, protein fragments, genes or gene fragments prepared from, for example, *Staphylococcus aureus, Streptococcus pyogenes, Streptococcus pneumoniae, Neisseria meningitidis, Neisseria gonorrhoeae*, Salmonellae species, Shigellae species, *Escherichia coli*, Klebsiellae species, Proteus species, *Vibrio cholerae, Helicobacterpylori, Pseudomonas aeruginosa, Haemophilus influenzae, Bordetella pertussis, Mycobacterium tuberculosis, Legionella pneumophila, Treponema pallidum*, and Chlamydiae species, tetanus toxoid, diphtheria toxoid, influenza viruses, adenoviruses, paramyxoviruses, rubella viruses, polioviruses, hepatitis viruses, herpesviruses, rabies viruses, human immunodeficiency viruses, and papilloma viruses, in addition to protozoal parasites such as *Toxoplasma gondii, Pneumocystis carinii, Giardia lamblia, Trichomonas vaginalis, Isospora beeli, Balantidium coli, Blastocystis hominis*, and the various species of Entamoeba, Amebae, Plasmodium, Leishmania, Trypanosoma, Babesia, Cryptosporidium, Sarcocystis, and Cyclospora, as well as nematodes and helminths of the various species of trematodes, flukes, cestodes and visceral larvae.

Immunogens may be administered as therapeutic or prophylactic agents, either with or without a potentiating agent. A therapeutic immunogen is defined herein as one that alleviates a pathological condition or disease. Therapeutic agents that may be used in the present invention include, but are not limited to, immunogenic agents and gene therapy agents. A prophylactic agent is defined herein as one that either prevents or decreases the severity of a subsequently acquired disease or pathological process. An example of a prophylactic agent is a vaccine against a microbe causing an infectious disease. A potentiating agent is defined herein as one that enhances the antigenicity of other immunogens. A potentiating agent thus indirectly stimulates an immune response. An example of a potentiating agent is an adjuvant, defined herein as any biological or chemical substance which, when administered with an immunogen, enhances the immune response against the immunogen. Examples of adjuvants are inorganic salts such as aluminum hydroxide (alum), cytokines, and bacterial endotoxins such as cholera toxin B (CTB). Another example of a potentiating agent is a hapten, defined herein as a low molecular weight substance that itself is nonimmunogenic but becomes immunogenic when conjugated to a high molecular weight carrier. Other potentiating agents include bioadhesives, mucoadhesives and promoting agents.

Microsphere Formulations

As used herein and unless specifically indicated otherwise, all percentages are given in terms of the weight of the ingredient relative to the total weight of the microsphere. In one embodiment of the invention, an aqueous solution of the immunogen with an optional stabilizing agent to provide physical protection for the immunogen is formed. The aqueous immunogen solution will generally be from about 0.5% to about 10% by weight of the immunogen in the microsphere, with about 1% being preferred.

Stabilizing agents are generally therapeutically inactive, water soluble sugars that act to protect the immunogen during a step in the formulation of the immunogen and/or during a subsequent coating step. Examples of stabilizing agents include the sugars lactose, mannitol and trehalose. The stabilizing agent is added at a concentration of from about 0.1% to about 10%, with a concentration of about 5% being preferred. If the immunogen solution has a low viscosity, it may be desirable to add from about 1% to about 10% of polyvinyl pyrrolidone or other binding agents such as hydroxypropylcellulose or hydroxypropylmethylcellulose to bind the immunogen to the inert particle.

The solution of one or more immunogens and an optional stabilizing agent is then applied, for example by spraying, to a pharmaceutically inert material substrate, hereinafter termed an inert particle. The inert particle may encompass a variety of shapes and forms such as a bead, a sphere, a powder, a crystal, or a granule. In one embodiment, a nonpareil, defined as a small round particle of a pharmaceutically inert material, may be used. One such nonpareil is available under the brand name NuPareils® (Crompton & Knowles Corp., Mahwah, N.J.). In other embodiments, a silica powder, sugar crystal or salt crystal may be used. The inert particle in whatever shape or form has a mesh size greater than about 35 mesh, preferably greater than about 40 mesh, and most preferably in the range of about 45 to 200 mesh.

Glatt® brand powder coater granulators such as the GPCG-1HS, GPCG-5HS, or GPCG-60HS fluid bed coaters are suitable for use to coat the immunogen onto the inert particle. Various other brands of Wurster type fluid bed coaters (NIRO, Vector, Fluid Air, etc.) are also suitable for use. Coating conditions and times vary depending on the apparatus and coating viscosity; however, coating must generally be conducted at temperatures less than about 50° C., and preferably less than about 35° C., to avoid denaturation of a protein immunogen.

The dry immunogen-coated inert particles are preferably also coated with one or more layers of acid stable polymers to form an enteric coating. This coating renders the immunogen resistant to degradation in the acid environment of the stomach. In addition, varying the composition and/or amount of the enteric coating may allow the enteric coating to dissolve, and thus release the immunogen, at a particular pH in the small intestine for an optimally selective T cell response. The coating of one or more polymers may be applied in a similar manner and with similar equipment as the coating steps previously described.

The enteric coating is preferably a water-based emulsion polymer such as ethylacrylate methacrylic acid copolymer, sold as Eudragit® L-30D (Hüls America Inc., Somerset, N.J.) with a molecular weight of about 250,000 and generally applied as a $30\%^{w/v}$ aqueous dispersion. Some examples of alternative polymer coatings are the solvent free Eudragit L/S 100 or hydroxypropylmethyl cellulose acetate succinate. The enteric coating allows the microencapsulated immunogen to be orally administered without being released from the microsphere until encountering a specific region of the gut. The chemical composition of the enteric coating may be formulated to dissolve, and thus release the immunogen, at a particular pH in the small intestine for an optimally selective T cell response. Alternatively, the enteric coating may be formulated to release the immunogen after encountering sufficient mechanical and/or chemical erosion.

The coating composition may be combined with a plasticizer to improve the continuity of the coating. Several well known plasticizers may be used, with triethyloitrate (MoIflex Inc., Greensboro, N.C.) preferred. Although plasticizers can be liquid, they are not considered to be solvents since they lodge within the coating and alter its physical characteristics but do not act to dissolve the protein immunogen. A plasticizer which dissolves or denatures the immunogen would be unacceptable.

Talc (about 3.0%) may be added to prevent the particles from sticking to each other. An antifoaming agent (about 0.0025%) such as sorbitan segquioleate (Nikko Chomicali Co. Ltd., Japan) or silicone can also be added. An antistatic agent (about 0.1%) such as Syloid 74FP (Davison Chemical Division, Cincinnati, Ohio.) can be added. The talc, antifoaming agent and antistatic agent are added only if needed.

The inert particles containing the immunogen, the optional stabilizing agent or agents and other formulation ingredients are dried and may be coated with the enteric coating as previously described. The coating solution is about 30% to about 75% polymer, about 0% to about 10% plasticizer, about 0% to about 3% talc, about 0% to about 0.0025% antifoaming agent, about 0% to 3% antistatic agent and water. It is generally preferable that there be no organic solvents., including alcohols and even glycols, present in the coating composition as organic solvents can denature the immunogen.

Potentiating Agents

In an alternative embodiment, a potentiating agent may be added to increase the immunogenicity of the protein. Examples of potentiating agents include adjuvants, bioadhesives, mucoadhesives, and promoting agents. Adjuvants work by either concentrating antigen at a site where lymphocytes are exposed to the antigen or by inducing cytokines which regulate lymphocyte function. The adjuvant may be either a biological compound, a chemical compound that is therapeutically acceptable, or a combination of a biological and chemical compound. Examples of chemical adjuvants are water dispersible inorganic salts such as aluminum sulfate, aluminum hydroxide (alum) and aluminum phosphate. Examples of biological adjuvants are endogenous cytokines such as granulocyte-macrophage colony-stimulating factor (GM-CSF), tumor necrosis factor-α (TNF-α), interleukin-2 (IL-2), interleukin-4 (IL-4), interleukin-12 (IL-12) and γ-interferon (IFNγ), microorganisms such as BCG (bacille Calmette-Guerin), *Corynebacterium parvum*, and *Bordetella pertussis*, bacterial endotoxins such as cholera toxin B (CTB), lipopolysaccharide (LPS), and muramyldipeptide (N-acetyl-muramyl-L-alanyl-D-isoglutamine [MDP]). Commercially available adjuvants such as DETOX-PC® are also available. Bioadhesives such as *Lycopersicon esculentum* lectin (tomato lectin, LT) and mucoadhesives such as Chitosans-like N-trimethyl chitosan chloride bind to sugars and form glycoconjugates at site-specific areas of the intestines. Promoting agents are defined herein as formulation ingredient(s) that promote uptake, transport or presentation of antigen(s), adjuvants, or haptens thereby enhancing the desired immune response. Examples of promoting agents are glycoproteins, lipoproteins, bile salts, fatty acids, phospholipids, glycolipids, triglycerides, and cholesterol, cyclodextrins, glycerol, among others. All of the above potentiating agents may be incorporated into the microsphere formulation singly, in combination, or as part of covalent or noncovalent complexes.

The potentiating agent may be added to the aqueous dispersion or solution of immunogen prior to coating onto the inert particle. Alternatively, the potentiating agent may be added to non-immunogen bound inert particles. Generally, about 1% to about 10% of potentiating agent is added. The potentiating agent may be bound to the same inert particle as the immunogen. Alternatively, the potentiating agent may be bound to a first inert particle and the immunogen may be bound to a second inert particle, such that the potentiating agent may be applied to non-immunogen bound inert particles.

Proposed Mechanism of Action

It has been found that microspheres produced from inert particles having a mesh size greater than about 35 mesh enhance and selectively stimulate T cytotoxic cells over other types of T cells. As shown in FIG. 1, the microspheres of the present invention have a potentiating agent-like effect and the extent of T cell stimulation increases with decreasing size of the inert particle of the microsphere. Mi(rospheres containing OVA with an inert particle mesh size greater than about 35 mesh (open bars) stimulated primary lymphocytes more than twice as much as microspheres containing both OVA and adjuvant with an inert particle mesh size less than about 35 mesh (solid bars). Microspheres containing OVA with a mesh size greater than about 35 mesh stimulated primary lymphocytes more than three times as much as parenterally administered OVA with adjuvant (hatched bars). This demonstrates that by using enteric coated immunogens attached to an inert particle having a mesh size greater than about 40 mesh, a potentiating agent-like effect in selecting for a T cytotoxic cell response is produced that is equivalent to the response produced using OVA administered with DETOX-PC® adjuvant. Thus, adding an adjuvant such as aluminum hydroxide (alum) or DETOX-PC® or other potentiating agent(s) to the microsphere formulation in certain cases may provide additional stimulation of a T cytotoxic cell population, and may allow a lower initial dose of immunostimulatory drug to generate an immune response equivalent to that obtained with a higher dose of immunostimulatory drug.

While the exact mechanism for these selective stimulations is unclear, one explanation may be that smaller enteric antigen coated particles provide an increase in contact points between the immunogen encapsulated therein and the appropriate immune cell receptor systems lying along the mammalian intestinal tract, particularly in the diffuse lymphatic tissue of Peyer's patches. These smaller particles also contain more of certain formulation ingredients on a per weight basis, some of which may enhance antigen presentation and delivery. Other explanations, however, may be possible.

Microsphere Dosing

In use, the microspheres of the present invention, comprising immunogen-bound inert particles having a mesh size greater than about 35 mesh and enteric coated with an optional potentiating agent, are administered in a dosing schedule and composition comprising various permutations of the above sizes and compositions to modulate an immune response. The microspheres are preferably administered orally such as by gavage or feeding, or may be administered parenterally such as by subcutaneous injection. Dosing may be consecutive or intermittent and at various times and in various formulations. As used herein, formulations encompass both the different percentage compositions and different physicochemical compositions of the microspheres, such as size, coatings, polymers, plasticizers, anti-stick agents, anti-foam agents, antistatic agents, potentiating agent(s) and excipients.

For example, an administered dose may contain a number of single inert particles with each inert particle containing one or more immunogens and, if added, the potentiating agent. If formulated as a single inert particle, the various single microspheres of the administered dose may have the same enteric coating or different enteric coatings, the same formulation or different formulations of polymers, plasticizers, binding agents, anti-stick agents, anti-foam agents, antistatic agents, potentiating agent(s) and excipients, and/or the same inert core composition and size or different inert core compositions and sizes. Alternatively, the dose may be formulated to contain a combination of inert particles with one or more immunogens and, if added, the potentiating agent(s) in separate inert particles. If formulated with the immunogen and potentiating agent(s) in separate inert particles, the separate microspheres of the administered dose may have the same enteric coatings or different enteric coatings, the same formulations or different formulations of polymers, plasticizers, binding agents, anti-stick agents, anti-foam agents, antistatic agents, potentiating agent(s) and excipients, and/or the same inert core compositions and sizes or different inert core compositions and sizes. These various combinations and permutations of inert particle size, inert particle composition, enteric coating, and formula composition help to achieve selective distribution and presentation of the antigen along the gut upon administration of the microspheres.

The microspheres may be placed in gel capsules for oral administration to humans or other mammals. Dosage will depend on the individual and the course of the therapy. For example, in treatment using the microspheres of the invention containing ragweed as the immunogen, the dosage would be about 0.03 to about 35 units in terms of a major allergenic protein, Amb-a-1, administered daily. Dosage for allergens may be different from the dosage used in immunotherapy by injection.

Applications

In use, the microspheres of the present invention containing an enteric coated immunogen and an optional potentiating agent have numerous applications. For example microspheres containing glycoproteins, proteins, protein fragments, peptides, or gene fragments from microorganisms, viruses or parasites would be a valuable prophylactic and/or therapeutic supplement to the typical antimicrobial, antiviral and antiparasitic agents administered to treat infectious diseases. As another example, a peptide fragment containing nondominant epitope(s) from the HER-2/neu oncogenic "self-protein" can be used as the immunogen in the microspheres of the invention to increase the efficacy of a cancer vaccine by breaking tolerance against overexpressed tumor proteins. This use would be especially valuable since HER-2/neu is a "self" protein and thus does not generate an immune response. By using a peptide containing nondominant epitope(s) rather than the whole protein as reported by Disis et al. (*J. Immunol.*, 1996:156, 3151–3158) in the microspheres of the invention, a cancer vaccine eliciting a T cytotoxic cell response targeting "self" tumor antigens would be produced. As still another example, the immunogen may be an allergen that increases a $T_H1$ type response and hence increase production of typical $T_H3$ cytokines such as y-interferon (IFN-y), tumor necrosis factor-β (TNF-β), and interleukin-2 (IL-2) which, in turn, may decrease inflammation in allergic conditions such as asthma.

The invention will be further appreciated in light of the following examples.

EXAMPLE 1

Tumor Cell Lines

The EL4 thymoma cell line (TIB-39) was obtained from American Type Culture Collection (ATCC, Rockville, Md.). The cells were maintained in culture using RPMI 1640 medium supplemented with 10% fetal calf serum (FCS) (HyClone Laboratories, Logan, Utah.), 15 mM HEPES buffer, 2 mM glutamine, 0.1 mM non-essential amino acids, 50 units/ml penicillin, 50 units/ml streptomycin, 1 mM sodium pyruvate (Biofluids, Rockville, Md.), and 50, μM 2-mercaptoethanol (Sigma, St. Louis, Mo.).

Antigens

Purified chicken egg ovalbumin (OVA) (grade V) was purchased from Sigma (St. Louis, Mo.). The $H-2K^b$ restricted peptide epitope of OVA protein, $OVA_{257-264}$ (SIINFEKL), was synthesized using FMOC chemistry on an Applied Biosystems Model 432A peptide synthesizer. The lyophilized product was resuspended in water at a concentration of 2 mg/ml, sterile filtered and stored at −70° C. The peptide was determined by high performance liquid chromatography to be greater than 90% pure.

OVA protein was coated onto inert particles and the antigen was encapsulated using an aqueous enteric coating system containing a biodegradable polymethacrylic acid copolymer (Eudragit L30D). The inert particles were NuPareils® measuring about 45 mesh.

Immunization

Six- to eight-week-old C57BL/6 ($H-2K^b$) female mice were obtained from Taconic Farms (Germantown, N.Y.). These animals were immunized either by subcutaneous injection with 30 μg OVA protein emulsified in DETOX-PC® adjuvant (RIBI ImmunoChem Research, Hamilton, Mont.), or orally via intubation into the back of the throat with microspheres containing 200, μg OVA. Control mice were orally fed a placebo microsphere. A series of three immunizations was performed on days 0, 14, and 28. Animals were euthanized three weeks following the final immunization.

Lymphoproliferation

Spleens were removed from immunized animals 21 days after their third immunization and were mechanically dispersed through a 70 μm nylon cell strainer (Falcon; Becton Dickinson, Franklin Lakes, N.J.) to yield a single cell suspension. Dead cells and erythrocytes were removed by centrifugation over a Ficoll-Hypaque gradient (d=1.119 g/cm). The recovered cell population was then enriched for T cells by passing the splenic mononuclear cells over nylon wool columns (Robbins Scientific Corp., Sunnyvale, Calif.). The enriched T cells were washed in complete medium (RPMI 1640 supplemented with 10% FCS, 15 mM HEPES buffer, 2 mM glutamine, 0.1 mM non-essential amino acids, 50 units/ml penicillin, 50 units/ml streptomycin, 50 μM 2-mercaptoethanol, and 1 mM sodium pyruvate) and dispersed into 96-well flat-bottom microtiter plates (Falcon; Becton Dickinson, Lincoln Park, N.J.) at a concentration of $1\times10^5$/well.

The T lymphocytes were then incubated in the presence of naive syngeneic splenocytes ($5\times10^5$/well) as antigen presenting cells (APC). Stimulated wells contained either OVA protein (100 μg/ml), $OVA_{257-264}$ peptide (100, μg/ml), or concanavalin A (Con A; 2.5 μg/ml). Control wells contained only T cells and APC in complete medium. All cultures were in a final volume of 200 μl and were incubated at 37° C. in 5% $CO_2$ for either 2 days (Con A) or 5 days (antigen stimulants). Cultures were pulsed with 1 μCi/well [$^3$H] thymidine (DuPont New England Nuclear, Wilmington, Del.) for the final 18 to 24 hours. Cultures were harvested using a PHD cell harvester (Cambridge Technology, Cambridge, Mass.) and incorporated radioactivity was quantitated by liquid scintillation spectroscopy (LS 6000IC, Duarte, Calif.). The results of triplicate wells were averaged and are reported as a stimulation index (SI) calculated by the following formula:

SI=stimulated wells (cpm)/control wells (cpm)

In vitro Stimulation of CTL

Primary CTL Cultures

Splenocytes ($25\times10^6$) harvested from each experimental group, pooled from the spleens of three animals per group, were incubated in 10 ml of complete RPMI (10% FCS, 15 mM HEPES buffer, 2 mM glutamine, 0.1 mM non-essential amino acids, 50 units/ml penicillin, 50 units/ml streptomycin, 50 μM 2-mercaptoethanol, and 1 mM sodium pyruvate) in upright 25 $cm^2$ flasks at 37° C. in 5% $CO_2$ in the presence of 5 μg/ml $OVA_{257-264}$ peptide.

Long-Term CTL Lines

Primary CTL cultures were harvested after seven days, and viable lymphocytes were recovered by centrifugation over a Ficoll gradient (d=1.08 g/ml; Organon Teknika Corp., Durham, N.C.). The recovered cells were restimulated in 24-well flat-bottom plates (Corning Costar Corp., Cambridge, Mass.) containing $0.5\times10^6$ lymphocytes, $5\times10^6$ irradiated (2,000 rads) syngeneic C57BL/6 spleen cells, 5 μg/ml $OVA_{257-264}$ peptide, and 10 units/ml recombinant human interleukin-2 (IL-2) (Cetus Corp., Emeryville, Calif.). Subsequent weekly restimulations of antigen specific CTL were performed in the same manner swith the exception of peptide dose. After 8 weeks of in vitro stimulation, the peptide concentration was reduced to 2 μg/ml.

Cytotoxicity Assays

Four hour $^{51}Cr$ release assays were performed. Target cells (tumor cells) were labeled with 50 μCi $Na^{51}CrO_4$/1× $10^6$ cells for 90 minutes. Target cells ($1\times10^4$) were labeled in 50 μl of complete RPMI medium and were added to the wells of a 96-well U-bottom plate (Corning Costar Corp.). When appropriate, target cells were incubated for 30 minutes at 37° C. in 5% $CO_2$ with one or more of the following before the addition of T cell effectors: $OVAL_{257-264}$ peptide, anti-CD8 antibody (supernatant from the 2.43 hybridoma), or anti-CD4 antibody (supernatant from the GK 1.5 hybridoma). Effector cells were added to the targets in 50 μl of complete medium. The plates were then incubated at 37° C. in 5% $CO_2$ for four hours. Following incubation, supernatants were harvested using Skatron harvesting frames (Skatron, Inc., Sterling, Va.). The release of radioactivity was quantitated using a gamma counter (Beckman Instruments) and the percent specific lysis was calculated using the equation:

$$\% \text{ specific lysis} = \frac{\text{experimental (cpm)} - \text{spontaneous release (cpm)}}{\text{maximum release (cpm)} - \text{spontaneous release (cpm)}} \times 100$$

Results were reported as the mean plus or minus the standard error of the mean of triplicate cultures.

Spontaneous release was calculated from wells to which 1 00 ml of medium had been added in the absence of T cell effectors. Maximum release was calculated from wells to which a solution of 2% Triton X-100 was added.

Flow Cytometry

Lymphocytes were harvested and washed three times with cold Dulbecco's phosphate-buffered saline (DPBS) containing $Ca^{2+}$ and $Mg^{2+}$ supplemented with 5% fetal bovine serum (FBS). Cells were incubated on ice for 45 minutes with either fluorescein isothiocyanate (FITC)-conjugated anti-mouse CD2, CD3, CD4, CD8, CD28, CD11a/CD18, and $\alpha/\beta$ T cell receptor (TCR), or the appropriate isotype control FITC-conjugated rat IgG2aK, rat IgG2b$\lambda$, or hamster IgG antibody (PharMingen, San Diego, Calif.), and then washed twice with DPBS solution free of $Ca^{2+}$ and $Mg^{2+}$. Data from 10,000 live cells/sample were analyzed using flow cytometric analysis as known to one skilled in the art with a Becton Dickinson FACScan® flow cytometer using an excitation wavelength of 488 nm and a band pass filter of 530 nm.

Lymphoproliferative Analysis

Figure 2A:
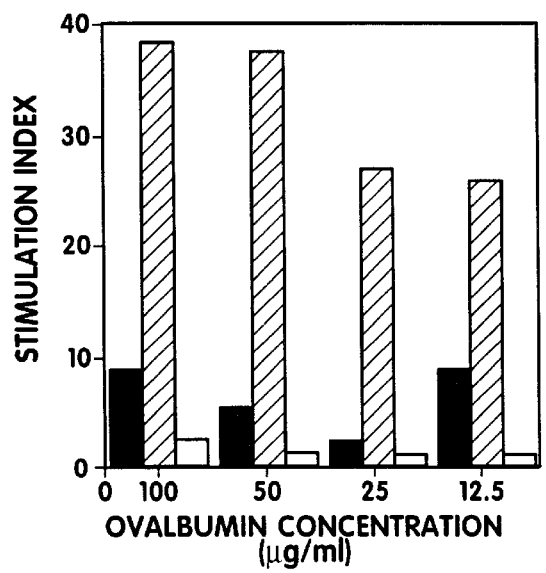
FIG. 2A is a graph of the results of a lymphoproliferative analysis using either microspheres containing OVA, OVA in adjuvant, or placebo microspheres.
Figure 2B:
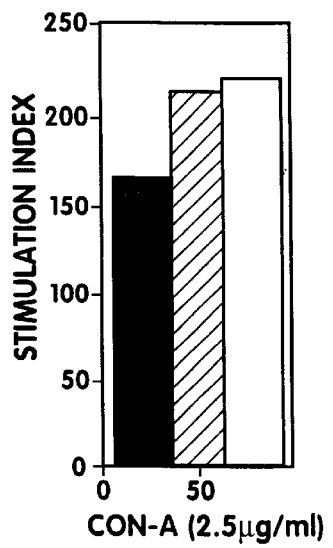
FIG. 2B is a graph of the results using concanavalin A (Con A) nonspecific mitogen stimulation.

FIG. 2A and FIG. 2B show the results of a lymphoproliferative analysis. As shown in FIG. 2A, and to determine if oral immunization with the model protein OVA could result in the activation of a cellular immune response, C57BL/6 mice were immunized three times with enterocoated microspheres containing OVA protein (microsphere-OVA) at concentrations of 12.5 µg/ml, 25 µg/ml, 50 µg/ml and 100 µg/ml (hatched bars). To compare the immune response generated following oral immunization with OVA to that of parenteral immunization with the same antigen, OVA protein was emulsified in DETOX-PC® adjuvant and administered subcutaneously to a second group of C57BL/6 mice (solid bars). A third group of C57BL/6 mice received a placebo microsphere by oral administration (open bars). Lymphocyte proliferation was assessed by measuring [$^3$H] thymidine incorporation.

As shown in FIG. 2A, T cells from mice receiving 100 µg/ml microsphere-OVA orally had a stimulation index of 38.3, while T cells from mice immunized with OVA protein in adjuvant had a stimulation index of 9.1. Naive splenocytes did not proliferate in the presence of OVA protein. As shown in FIG. 2B, lymphocytes from each group showed strong stimulation indices upon non-specific mitogen stimulation with 2.5 µg/ml Con A.

EXAMPLE 2

A CTL immune response in mice that had been orally immunized with enterocoated microsphere-OVA generated an antigen-specific T cell line. Purified splenocytes from mice immunized with OVA, either orally in microspheres or, as a control, subcutaneously in an emulsion with DETOX-PC® adjuvant, were cultured in vitro in the presence of OVA$_{257-264}$ peptide, irradiated syngeneic splenocytes as APC, and IL-2. The cell lines were maintained on seven-day cycles of in vitro stimulation (IVS). The ability of the cell lines to lyse target cells in an antigen-dependent manner was evaluated five days into the IVS cycle using a four-hour $^{51}$Cr release assay. The EL4 (H-2K$^b$) cell line was used as a target cell in these assays. EL4 cells were pre-pulsed with OVAL$_{257-264}$ peptide prior to the addition of T cell effector cells into the assay. All data are at a 20:1 effector:target ratio.

Figure 3A:
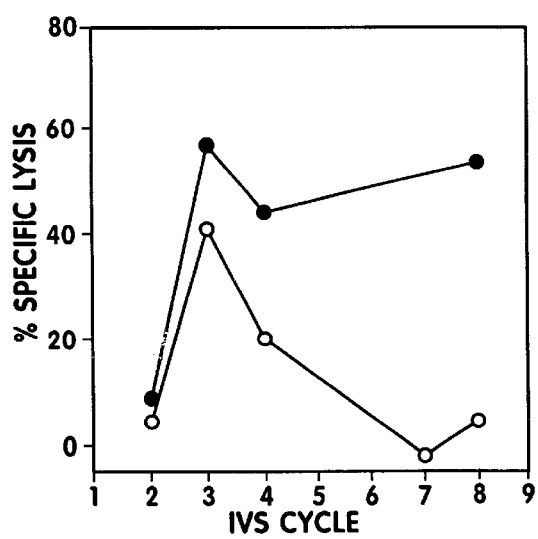
FIG. 3A is a graph of the results from in vitro stimulation with microspheres containing OVA.
Figure 3B:
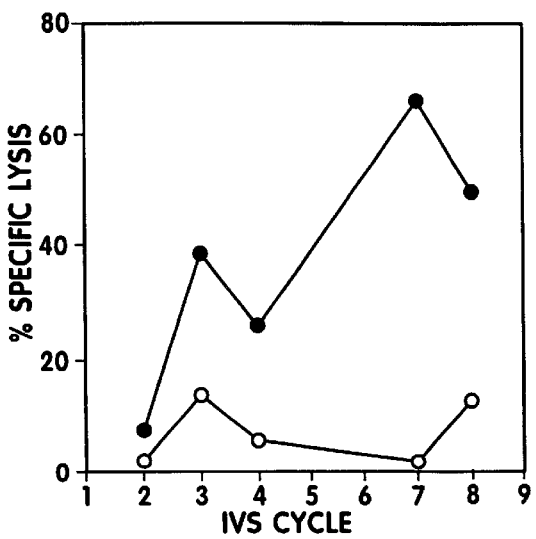
FIG. 3B is a graph of the results using Con A nonspecific mitogen stimulation.

As shown in FIG. 3A and FIG. 3B, the emergence of antigen-specific lysis was evident after only three cycles of IVS. FIG. 3A shows T cell effectors from mice immunized by subcutaneous administration of OVA emulsified in DETOX-PC® adjuvant. FIG. 3B shows T cell effectors from mice immunized by oral administration of microsphere-OVA. Closed circles represent EL4 cells pre-pulsed with 25 µg/ml OVAL$_{257-264}$ CTL epitope peptide. Open circles represent non-pulsed EL4 cells.

While antigen-specific lysis was evident after three cycles of IVS, non-specific lysis of EL4 cells was also observed at this time point. Following six cycles of IVS, non-specific lysis of EL4 cells had dropped substantially (about 10% to about 20%). At the eighth cycle of IVS, both cell lines were approaching higher (about 50% to about 60%) levels of antigen-specific lysis with very low levels (less than about 10%) of non-specific lysis.

Figure 4:
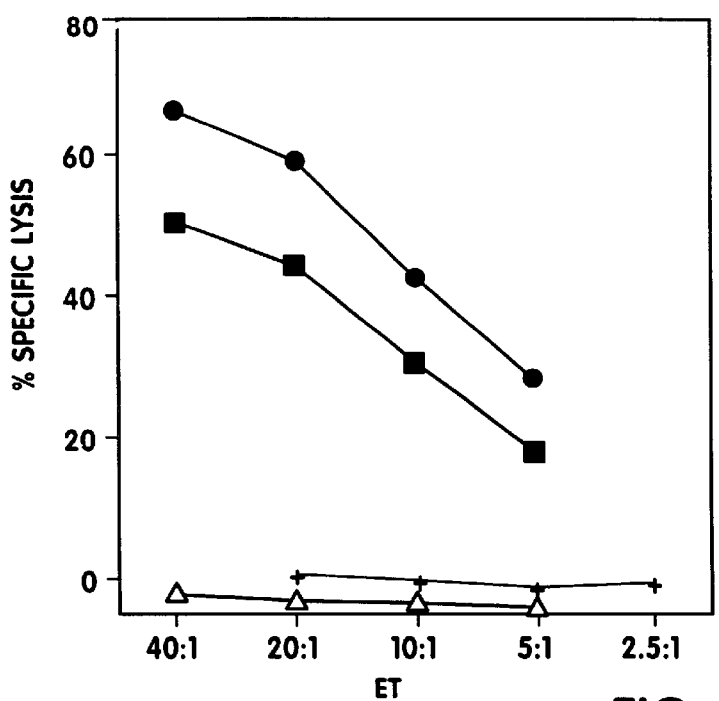
FIG. 4 is a graph of cytotoxic T lymphocyte responses at different effector:target ratios.

As shown in FIG. 4, the strength of the CTL lines derived from immunized animals was evaluated as a function of effector:target ratio. EL4 cells were pre-pulsed with 25 µg/ml OVAL$_{257-264}$ peptide. Closed circles represent microsphere-OVA. Closed squares represent OVA emulsified in DETOX-PC® adjuvant. Crosses represent placebo microspheres and open triangles represent non-specific $^{51}$Cr uptake of non-peptide pulsed EL4 cells. Both CTL lines could be titrated through a range of effector:target ratios. When splenocytes from animals that had been administered placebo microspheres were cultured under the same conditions as the experimental cell lines, they could not be in vitro activated to recognize peptide pulsed target cells. This observation also demonstrated that the experimental cell lines acquired their antigen specificity via in vivo activation following oral or parenteral immunization with OVA, and not as a result of in vitro culture conditions.

Figure 5A:
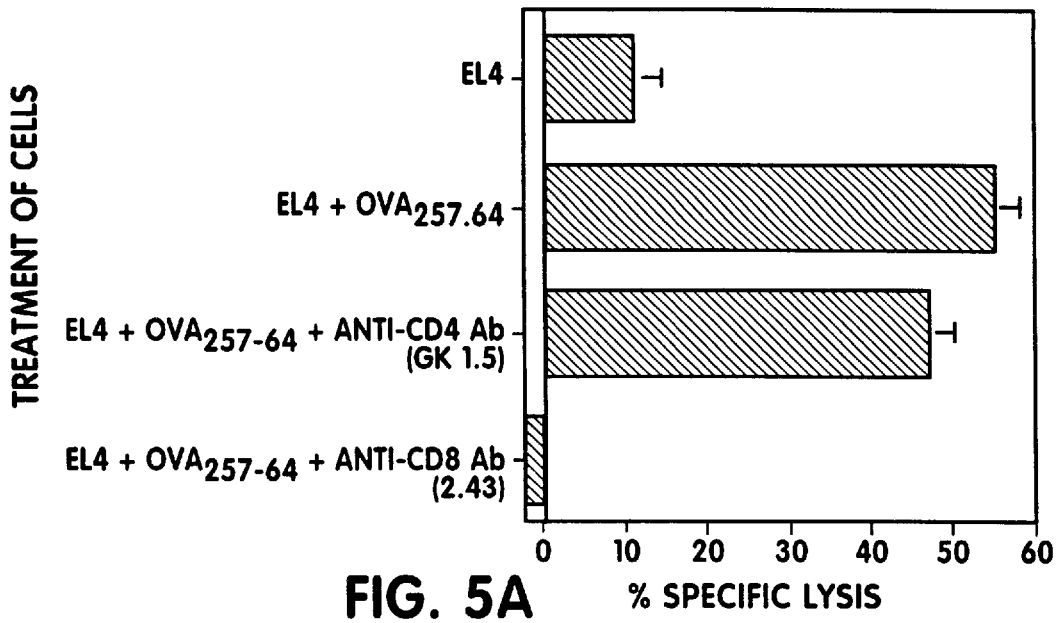
FIG. 5A is a graph of the results of antibody blocking experiments for microspheres containing OVA.
Figure 5B:
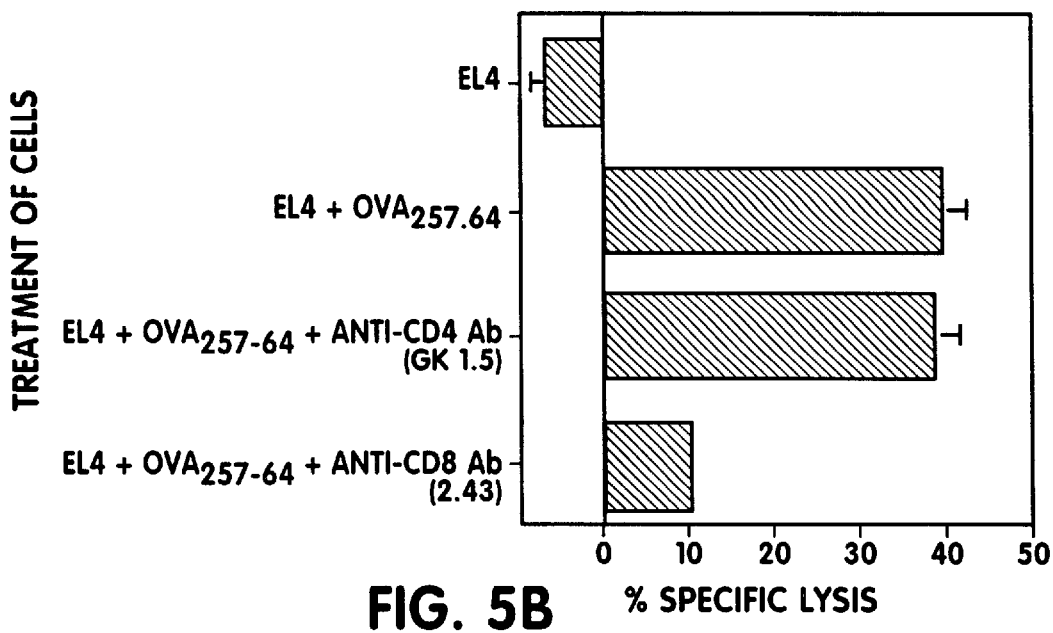
FIG. 5B is a graph of the results using Con A nonspecific mitogen stimulation.

To confirm that the cell lines derived from each group of immunized animals lysed tumor cells in a CD8$^+$ T cell dependent fashion, antibody blocking experiments were performed. FIG. 5A and FIG. 5B show CD8$^+$ T cell dependence of antigen-specific target cell lysis. FIG. 5A shows a four hour $^{51}$Cr release assay at a 40:1 effector:target ratio using OVAL$_{257-264}$ pulsed EL4 target cells, to determine dependence of CD8$^+$ to cells on the observed target cell lysis by the CTL line derived from animals immunized by subcutaneous administration of OVA in adjuvant. FIG. 5B shows a four hour $^{51}$Cr release assay at a 20:1 effector: target ratio using OVA$_{257-264}$ pulsed EL4 target cells, to determine dependence of CD8$^+$ T cells on the observed target cell lysis by the CTL line derived from animals immunized by oral administration of microsphere-OVA.

As shown in FIG. 5A and FIG. 5B, in four hour $^{51}$Cr release assays, the supernatant from either the hybridoma GK1.5, secreting anti-CD4 antibody, or the hybridoma 2.43, secreting anti-CD8 antibody, was incubated with T cells prior to their addition to OVAL$_{257-264}$ pulsed EL4 target cells. In the presence of anti-CD8 antibody, the antigen-speoific tumor cell lysis was inhibited. Conversely, the presence of anti-CD4 antibody resulted in minimal (about 1% to about 10%) inhibition of T cell mediated antigen-specific cell lysis. The lytic activity of both T cell lines was eliminated when the T cells were pre-incubated with the supernatant of the 2.43 hybridoma that contains anti-CD8 antibody. Preincubation of the T cells with GK 1.5 hybridoma supernatant containing anti-CD4 antibody did not cause a major decrease in the lytic activity of the cell line.

FACS Analysis

The presence of T cell surface markers on OVA-derived cell lines was analyzed by flow cytometry. Table 1 shows phenotypic characterization of T cell lines following eight cycles of IVS. The cell lines were derived from splenocytes of mice that had been immunized with either microsphere-OVA or OVA in adjuvant as previously described.

TABLE 1

| Cellular Determinant | % Positive Cells (mean fluorescence intensity) | |
|---|---|---|
| | Ovalbumin-DETOX-PC ® | Microsphere Ovalbumin |
| CD3 | 95.55 (23.32) | 99.18 (77.94) |
| CD4 | 57.69 (62.37) | 8.02 (52.63) |
| CD8 | 49.68 (138.16) | 92.69 (174.30) |
| CD2 | 78.82 (19.98) | 69.14 (26.37) |
| CD28 | 12.98 (32.01) | 60.99 (18.38) |
| CD11a/CD18 | 99.58 (157.77) | 98.22 (89.00) |
| α/β TCR | 64.34 (16.53) | 77.33 (21.78 |

As shown in Table 1, both cell lines had a population of greater than about 95% T cells as identified by the CD3 cell surface molecule. The T cell line derived from lymphocytes cultured from mice immunized with OVA in adjuvant contain ed 49.6% $CD8^+$ a T cells, and the cells, line derived from lymphocytes cultured from mice orally immunized with microsphere-OVA contained 92.7% $CD8^+$ T cells. Both cell lines were shown to express the costimulatory molecule receptors CD2 and CD28, in addition to the integrin molecule CD11a/CD18. The cultured T cells from both groups of immunized animals also expressed the usage of an α/β T cell receptor. These data help to illustrate that the T cells activated through oral microsphere immunization with the protein antigen OVA are phenotypically similar to the repertoire activated following parenteral immunization with the same antigen.

The microspheres o f the present invention modulate an immune response. The response may encompass a general enhanced production of $T_H1$ cells, $T^H2$ cells and cytotoxic T lymphocyte (CTL) subsets, or an enhanced shift from a $T^H2$ type response to a $T_H1$ type response, or an enhanced shift from a $T_H1$ type response to a $T^H2$ type response, or an enhanced differentiation of pre-CTL to CTL. The immunogen may be a peptide, a protein fragment, a protein, a DNA, and/or an RNA, and may be a gene, a gene fragment or a vaccine. The therapeutic or prophylactic agents encompass immunogens, immunotherapy agents or gene therapy agents, either separately or in combination, that may be orally delivered in enteric microencapsulated formulations as bound to an inert particle having a size greater than about 35 mesh and in the form of a substrate bead, granule, powder, or crystal.

It will be appreciated that the delivery system composition and methods disclosed herein can be used prophylactically and therapeutically in a wide array of conditions. Thus, the embodiments of the present invention shown and described in the specification are only preferred embodiments of the inventor who is skilled in the art and are not limiting in any way. Various changes, modifications or alterations to these embodiments may be made or resorted to without departing from the spirit of the invention and the scope of the following claims.

What is claimed is:

1. A method of inducing an immune response in a mammal comprising administering a microsphere comprising an immunogen bound to an inert particle to a small intestine of said mammal, said inert particle having a mesh size greater than about 35 mesh.

2. The method of claim 1 wherein said microsphere is administered orally and said microsphere comprises an enteric coated microsphere.

3. The method of claim 1 wherein said microsphere is administered in a gel capsule.

4. The method of claim 1 wherein said immunogen is selected from the group consisting of a peptide, a protein fragment, a protein, a gene, a gene fragment, a DNA, an RNA and combinations thereof.

5. The method of claim 1 wherein said immunogen is a vaccine.

6. The method of claim 1 further comprising administering a potentiating agent bound to an inert particle, said inert particle selected from the group consisting of an immunogen-bound inert particle and a non-immunogen bound inert particle.

7. The method of claim 1 wherein a plurality of microspheres are administered to selectively induce the immune response.

8. The method of claim 7 wherein said plurality of microspheres have compositions selected from the group consisting of different inert particle sizes, different inert particle compositions, different enteric coatings, different formulations and combinations thereof.

9. The method of claim 1 wherein said microsphere comprising said immunogen induces an increase in the number of T lymphocytes.

10. The method of claim 9 wherein said microsphere containing said immunogen induces an increase in a cell population selected from the group consisting of a $T^H1$ lymphocyte, a cytotoxic T lymphocyte (CTL), and combinations thereof.

11. The method of claim 1 wherein said inert particle has a mesh size greater than about 40 mesh.

12. The method of claim 1 where said immunogen is contained on an inert particle selected from the group consisting of a nonpareil, a silica powder, a salt crystal and a sugar crystal.

13. A method of inducing an immune response in a mammal comprising orally administering to said mammal at least one microsphere each comprising an enteric-coated inert particle containing a protein imnunogen, said particle having a mesh size greater than about 40 mesh.

14. The method of claim 13 further comprising administering a potentiating agent bound to an inert particle, said inert particle selected from the group consisting of an immunogen-bound inert particle and a non-immunogen bound inert particle.

15. The method of claim 13 wherein a plurality of microspheres are administered to selectively induce the immune response.

16. The method of claim 15 wherein said microspheres have compositions selected from the group consisting of different inert particle sizes, different inert particle compositions, different enteric coatings, different formulations and combinations thereof.

17. The method of claim 13 wherein the immune response comprises an increase in a T lymphocyte population.

18. The method of claim 13 wherein the immune response comprises an increase in a cell population selected from the group consisting of a $T_H1$ lymphocyte, a cytotoxic T lymphocyte (CTL), and combinations thereof.

* * * * *